United States Patent
Wee

(10) Patent No.: US 7,631,543 B2
(45) Date of Patent: Dec. 15, 2009

(54) METHOD AND APPARATUS FOR MEASURING THE COMPOSITION AND WATER SALINITY OF A MULTIPHASE MIXTURE CONTAINING WATER

(75) Inventor: Arnstein Wee, Oslo (NO)

(73) Assignee: Multi Phase Meters AS, Forus (NO)

( * ) Notice: Subject to any disclaimer, the term of this patent is extended or adjusted under 35 U.S.C. 154(b) by 192 days.

(21) Appl. No.: 11/660,177

(22) PCT Filed: Aug. 19, 2005

(86) PCT No.: PCT/NO2005/000301

§ 371 (c)(1),
(2), (4) Date: Jun. 15, 2007

(87) PCT Pub. No.: WO2006/019311

PCT Pub. Date: Feb. 23, 2006

(65) Prior Publication Data

US 2007/0279073 A1    Dec. 6, 2007

(30) Foreign Application Priority Data

Aug. 20, 2004  (NO) .................................. 20043470

(51) Int. Cl.
*G01N 30/62* (2006.01)
*G01N 30/95* (2006.01)
*G01N 37/00* (2006.01)
(52) U.S. Cl. ...................... 73/61.61; 324/637; 324/638; 324/639; 324/640; 324/641; 324/642; 324/643; 324/644; 324/645; 324/646
(58) Field of Classification Search .......... 324/637–646
See application file for complete search history.

(56) References Cited

U.S. PATENT DOCUMENTS 4,458,524 A * 7/1984 Meador et al. ............. 73/61.43

(Continued)

FOREIGN PATENT DOCUMENTS

NO      20010616      2/2005

(Continued)

OTHER PUBLICATIONS

International Search Report dated Dec. 13, 2005.

(Continued)

*Primary Examiner*—Hezron Williams
*Assistant Examiner*—Rachel Black
(74) *Attorney, Agent, or Firm*—Nields, Lemack & Frame, LLC

(57) ABSTRACT

A method for determining the composition and water salinity of a multi-component mixture of a gas and at least one liquid, including water, in a pipe (1), the method comprising the following steps: a. electromagnetic phase measurements are performed between two receiving antennas (4) located at different distances from a sending antenna (3), b. based on an empirically determined constant(s) and the above measurements, the effective and imaginary dielectric constants are determined, c. the mixture density is determined, d. the temperature and pressure are determined e. based on the knowledge of densities, effective dielectric constants and imaginary dielectric constants of the components of the fluid mixture and the results of the above steps a-d, the volume fractions of the gas and liquid or liquids of the fluid mixture and salinity of the water are calculated. An apparatus for performing the method is also disclosed.

15 Claims, 6 Drawing Sheets

U.S. PATENT DOCUMENTS

Figure 1:
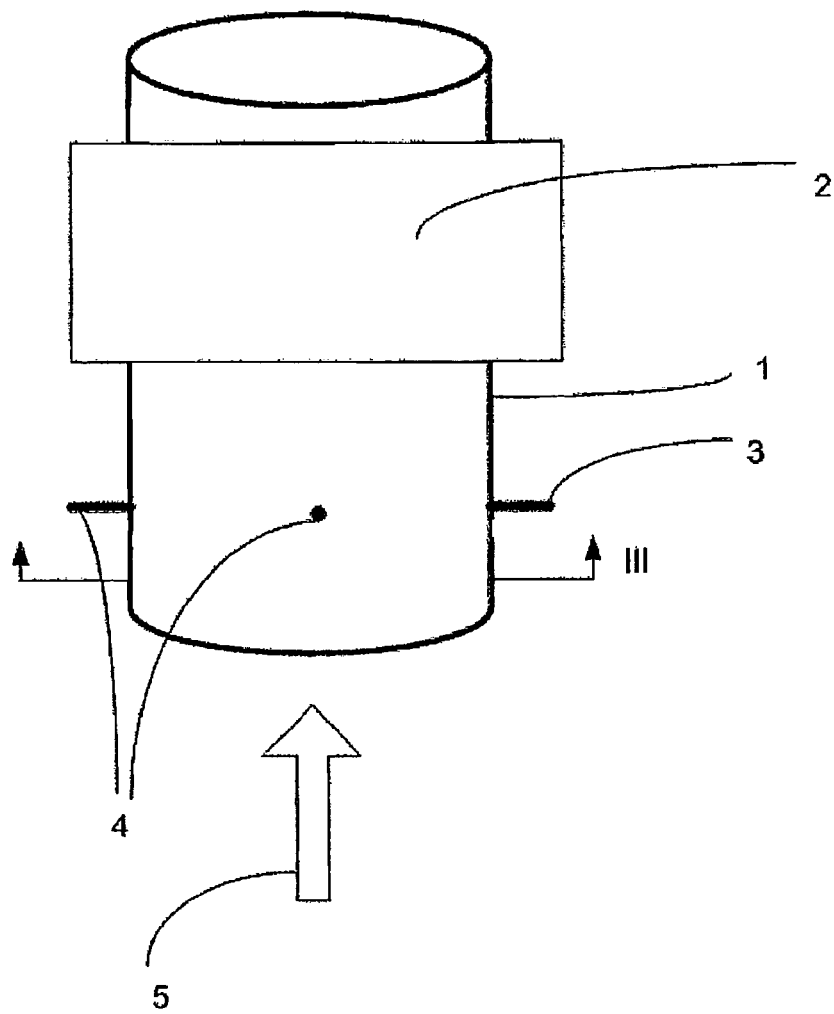

| | | | |
|---|---|---|---|
| 4,902,961 A * | 2/1990 | De et al. | 324/640 |
| 5,103,181 A | 4/1992 | Gaisford et al. | 324/637 |
| 5,455,516 A | 10/1995 | Jean et al. | 324/639 |
| 5,576,974 A * | 11/1996 | Marrelli et al. | 702/179 |
| 6,466,035 B1 | 10/2002 | Nyfors et al. | 324/634 |
| 6,655,221 B1 * | 12/2003 | Aspelund et al. | 73/861.04 |
| 6,831,470 B2 * | 12/2004 | Xie et al. | 324/693 |

FOREIGN PATENT DOCUMENTS

WO  03/034051  4/2003

OTHER PUBLICATIONS

Ber. Bunsenges. Phys. Chem. 95 (1991) No. 8; J.Barthel, et al.; "A Computer-Controlled System of Transmission Lines for the Determination of the Complex Permittivity of Lossy Liquids between 8.5 and 90 GHz."

Journal of Research of the National Bureau of Standards; vol. 56, No. 1, Jan. 1956; Research paper 2641; C.G. Malmberg et al.; "Dielectric Constant of Water from 0° to 100° C".

Report from Boeing/AER investigation for CMIS (Imaginary dielectric constant for fresh water); Thomas Meissner et al.; "The Complex Dielectric Constant of Pure and Sea Water from Microwave Satellite Observations".

Aqueous Dielectrics (1973), p. 29; J.B. Hasted; "The Water Molecule and Dielectric Theory".

Am.Chem Soc. 72 2844; G.C. Akerlof et al.; "The Dielectric Constant of Water at High Temperatures and in Equilibrium with its Vapor".

* cited by examiner

METHOD AND APPARATUS FOR MEASURING THE COMPOSITION AND WATER SALINITY OF A MULTIPHASE MIXTURE CONTAINING WATER

The present invention relates to a method and apparatus for measuring the fractions and water salinity of a multiphase mixture based on a measurement of the complex dielectric constant and density of the multiphase mixture. The complex dielectric constant is determined by measuring the frequency location of a phase shift between two receiving antennas and the spread of the phase shift divided by the frequency location of the phase shift. The method is particularly suitable for high precision measurement of the volume fraction and salinity of small amounts of water dispersed in a hydrocarbon continuous mixture such as measurement of water fraction and water salinity of a hydrocarbon wet gas stream (typical water fraction for a wet gas stream is in the order of 0.001-0.5% of pipeline volume). The method is not useable for measurement of the complex dielectric constant of a highly lossy medium such as a multiphase mixture where hydrocarbons are dispersed in water and the salinity of the water is above approximately 0.5% NaCl by weight.

A flowing fluid mixture of oil water and gas or condensate water and gas is a common occurrence in the oil industry being a product of an unprocessed well stream. Such a well stream is often referred as a multiphase flow mixture where oil, water and gas are referred to as individual phases or fractions.

When the gas fraction of the well stream is above 90% gas, the well is commonly referred to as a wetgas well. Wetgas wells may also be referred to as a gas/condensate well where the condensate is condensed liquid from the gas. The composition of a gas/condensate well could typical be 98% gas, 1.9% condensate and 0. 1% liquid fresh water which have been condensed from the gas. The formation water in the hydrocarbon reservoir is typical saline water and its salinity is usually known to the operator. Under normal situations, the well should not produce any formation water. In fact, formation water in the pipeline can cause hydrate and scale formation and could also cause severe pipeline corrosion. If the amount of formation and fresh water (also referred as total water fraction) in a well is known to the field operator, chemical inhibitors can be injected into the well stream in order to limit the unwanted effects due to the water or the production rate from the well can be changed in order to minimize the formation water production. It is of particular interest to measure the formation and fresh water content of remotely operated subsea wells since the cost of the pipelines in such an installation is severe. By measuring the total water (formation water plus fresh (condensed) water) fraction and water salinity, the fresh water and formation water fraction of the well can be determined since the salinity of the formation water is known to the operator. In order to fulfill the requirements of the field operator, an instrument for measuring the total water fraction and water salinity of the wells would need to be able to perform reliable and repeatable measurements of the water fraction and water salinity with formation water fractions as small as a few per thousand of the total area in the pipeline.

Microwaves are widely used for measurement of composition and water salinity of a multiphase mixture. U.S. Pat. No. 4,458,524 (1984) discloses a multiphase flow meter that measures the dielectric constant (permittivity), density, temperature and pressure. Such device uses phase shift between two receiving antennas to determine the dielectric constant. Other techniques are further known being based on resonance frequency measurement. Examples of such techniques are disclosed in W03/034051 and U.S. Pat. No. 6,466,035. U.S. Pat. No. 5,103,181 describe a method based on measurement of constructive and destructive interference patterns in the pipe.

However, none of the above described methods are able to measure the complex dielectric constant such that the water salinity of the multiphase mixture can be determined.

It is well known that the complex dielectric constant of a media can be measured by measuring the phase shift and attenuation of an electromagnetic wave through the media. U.S. Pat. No. 4,902,961 describe a method for measuring complex dielectric constant based on measurement of phase shift and power attenuation. The measurement is performed at two different (fixed) frequencies, one in the X-band and the other in the S-and. Since this method rely on power measurements for measuring the complex dielectric constant, it would not have the required sensitivity and stability in order to perform accurate measurement of water fraction and water salinity of a hydrocarbon wetgas stream. NO 200 10 616 discloses a method for measurement of the water conductivity of the continuous phase of a multiphase mixture based on a power and phase measurement at microwave frequencies. However, this method also relies on a power measurement and the method is not able to perform accurate measurement of the complex dielectric constant of hydrocarbon continuous mixture with a dispersed water phase.

It is the purpose of this invention to provide accurate measurement of the complex dielectric constant. It is the purpose of this invention to perform accurate measurements of the dispersed water fraction and water salinity of a hydrocarbon continuous medium. It is the purpose of this invention to perform accurate measurements of the oil, gas and water fraction and water salinity of a multiphase mixture containing small amounts of water and large amounts of gas which is typical for hydrocarbon wet gas streams.

The method according to the present invention compromises the following steps:
a. electromagnetic phase measurements are performed between two receiving antennas located at a different distance from a sending antenna,
b. based on an empirically determined constant(s) and the above measurements, the effective and imaginary dielectric constants are determined,
c. the mixture density is determined,
d. the temperature and pressure are determined
e. based on the knowledge of densities, effective dielectric constants and imaginary dielectric constants of the components of the fluid mixture and the result from the above steps a-d, the volume fractions of the gas and liquid or liquids of the fluid mixture and salinity of water are calculated.

The apparatus according to the invention is further characterized by the features as defined in the independent claim 8.

Dependent claims 2-7 and 9-12 define preferred embodiments of the invention.

Figure 2:
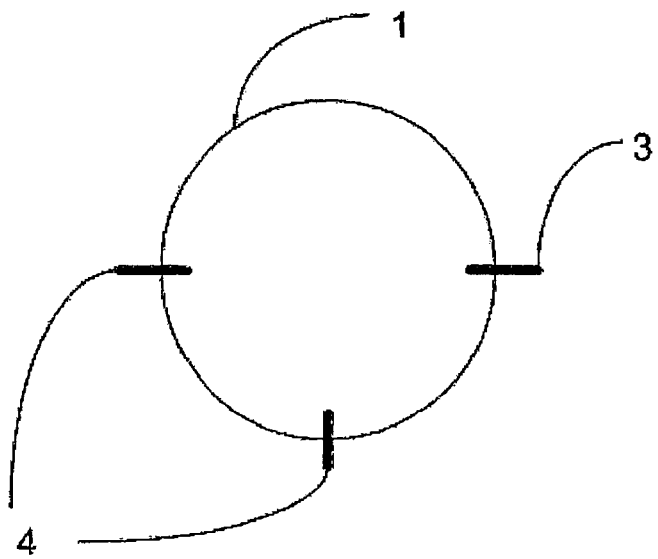
Figure 3:
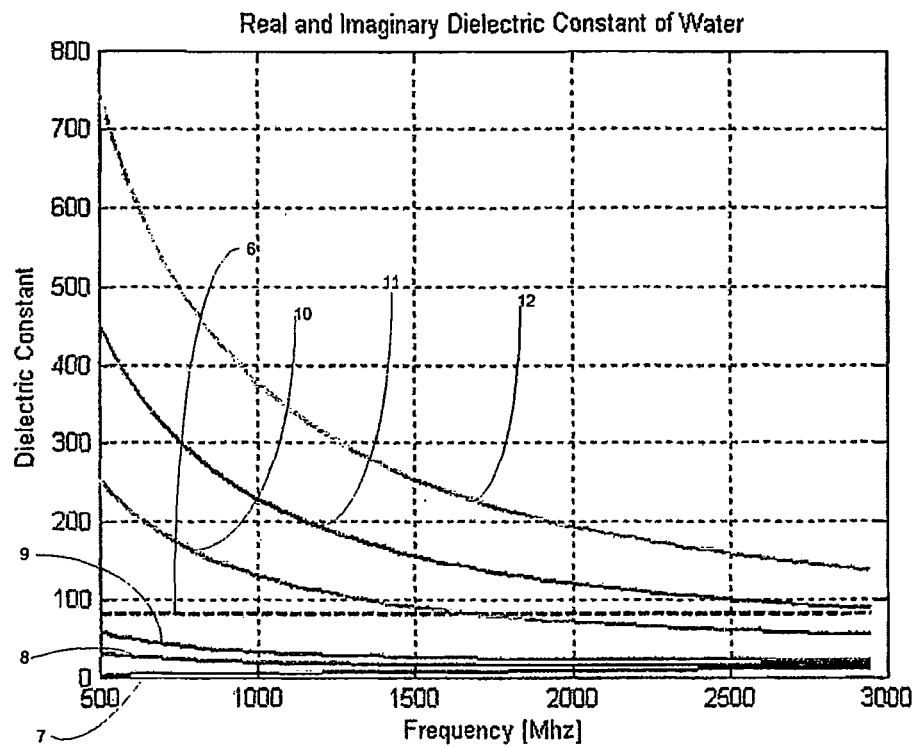
Figure 4:
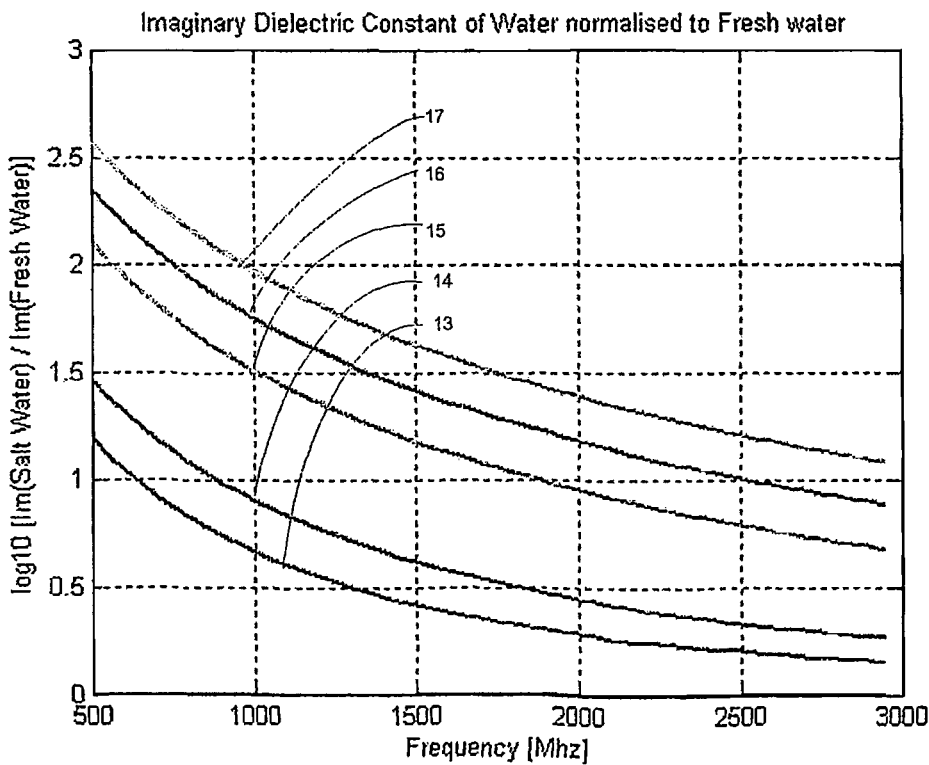
Figure 5:
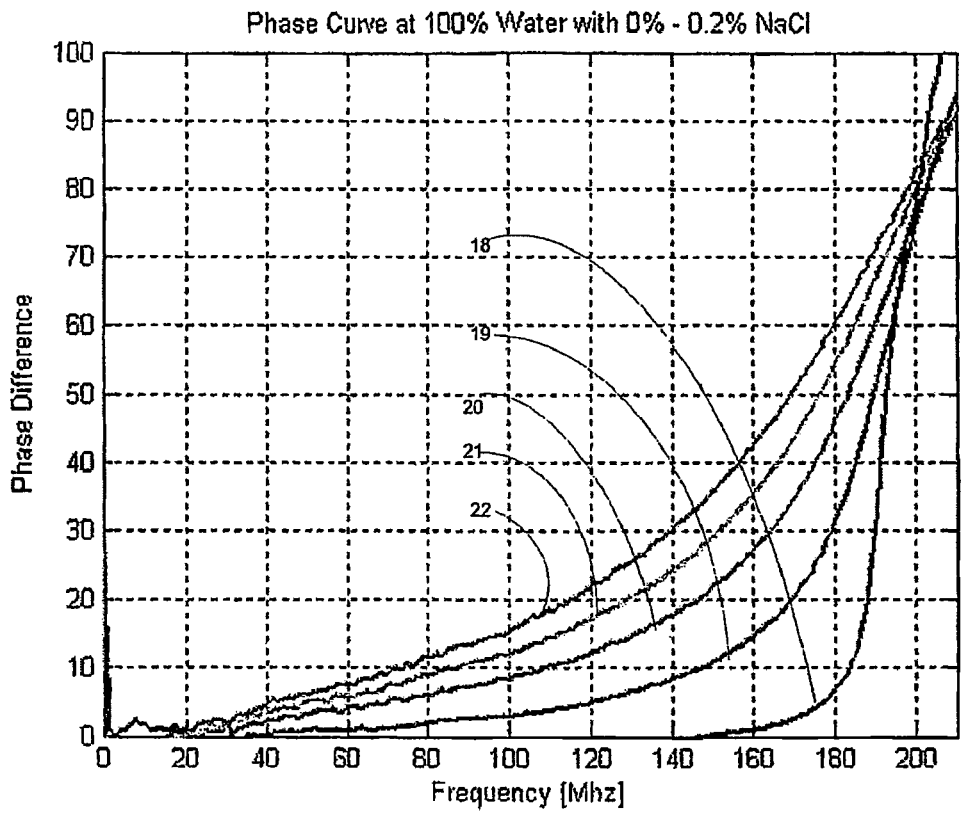
Figure 6:
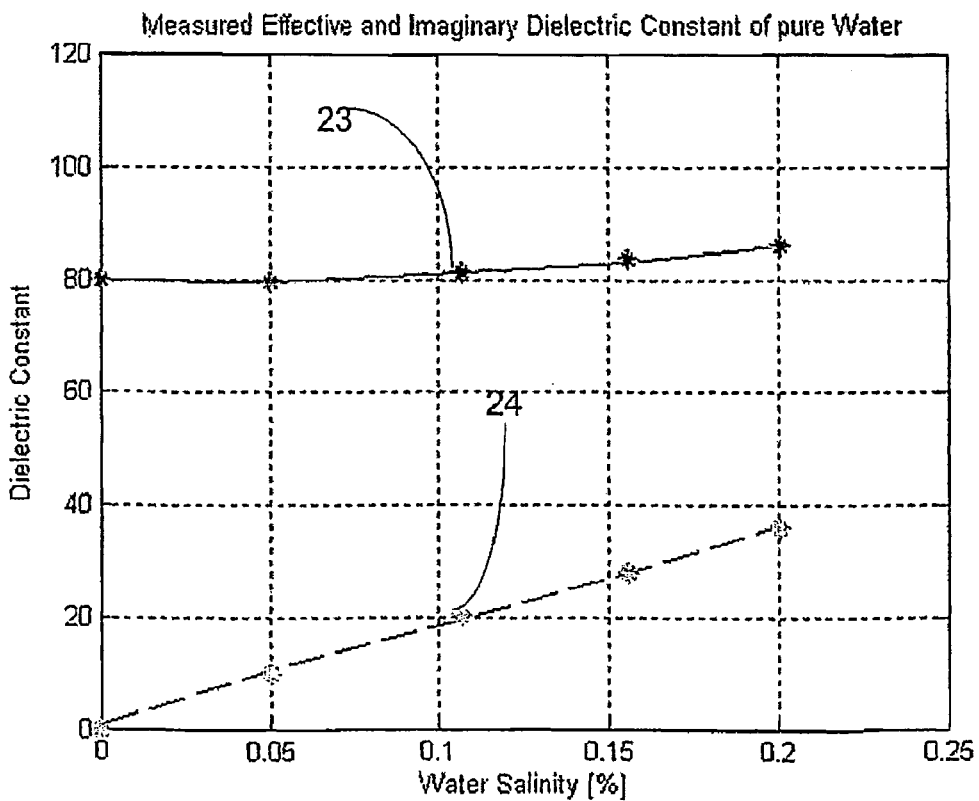
Figure 7:
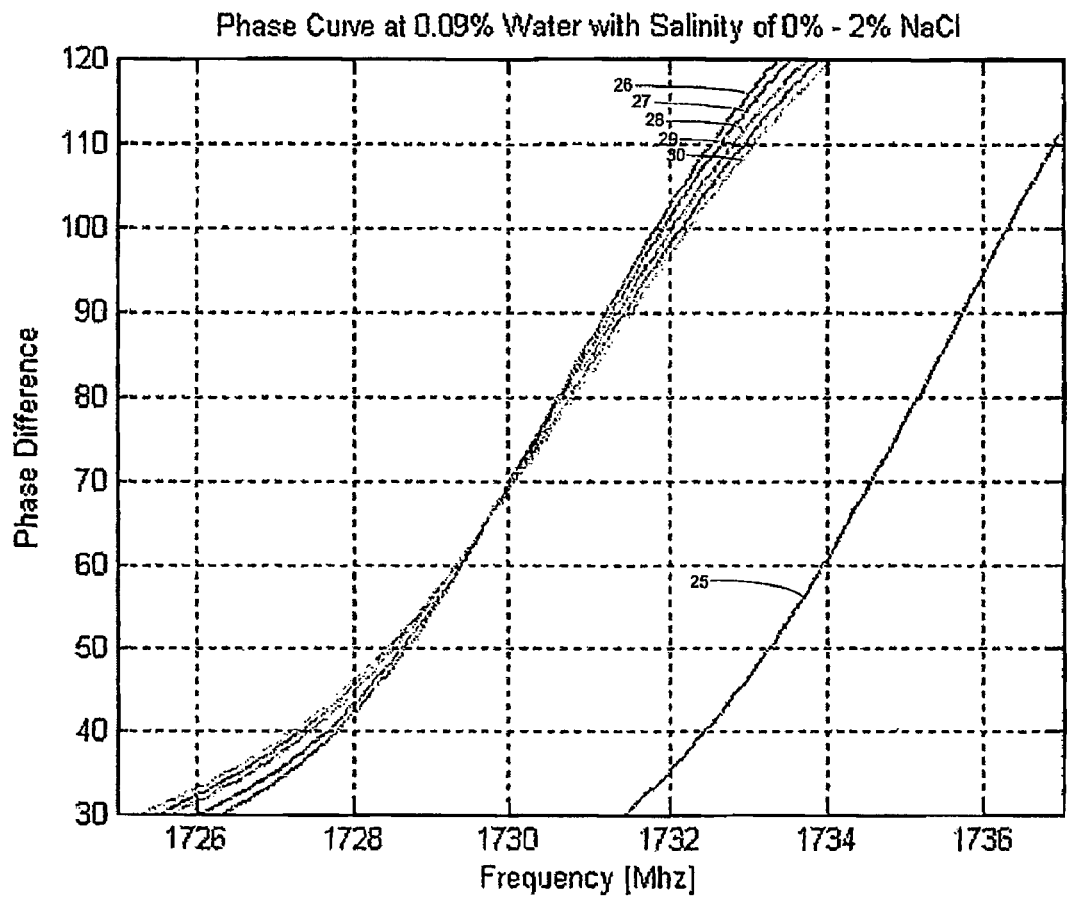
Figure 8:
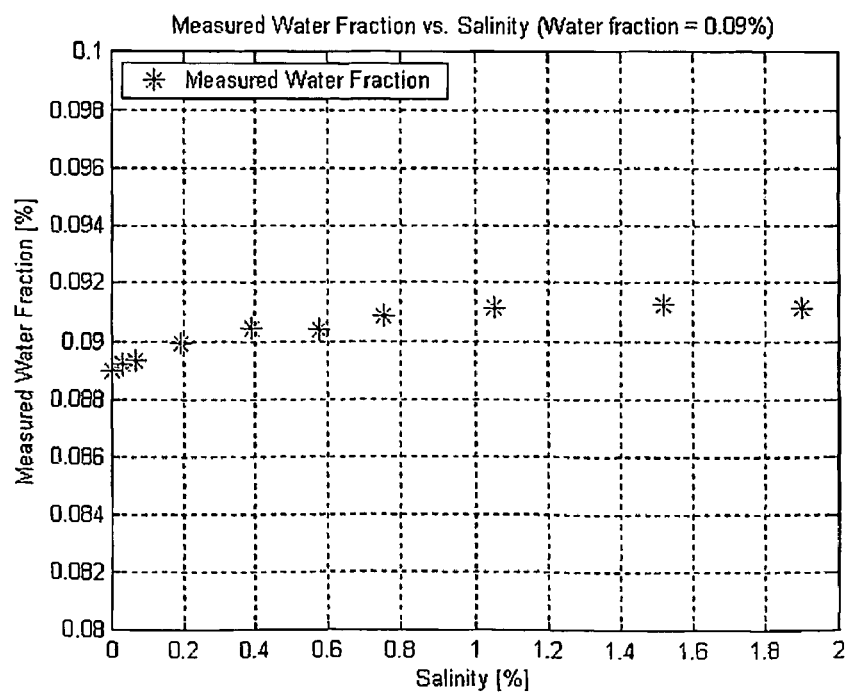
Figure 9:
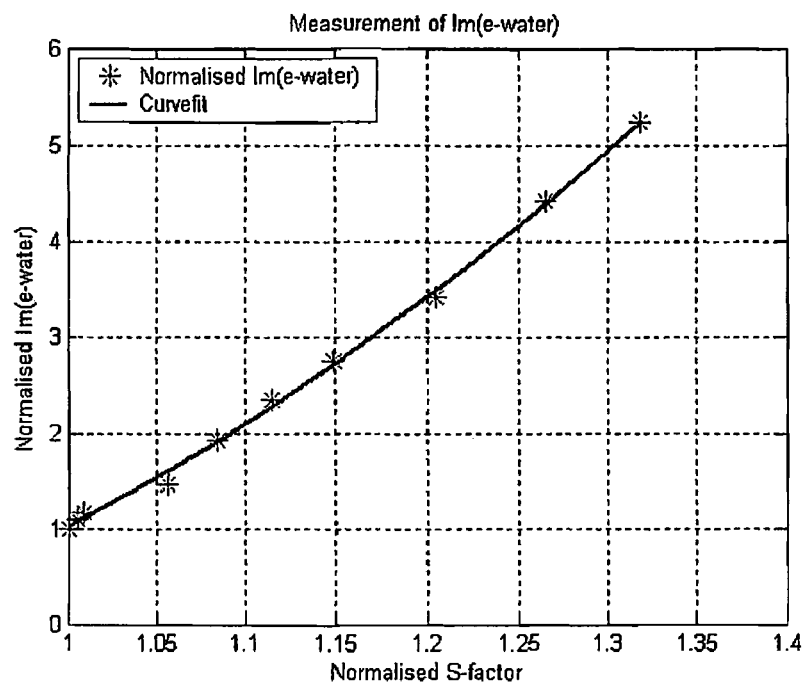
Figure 10:
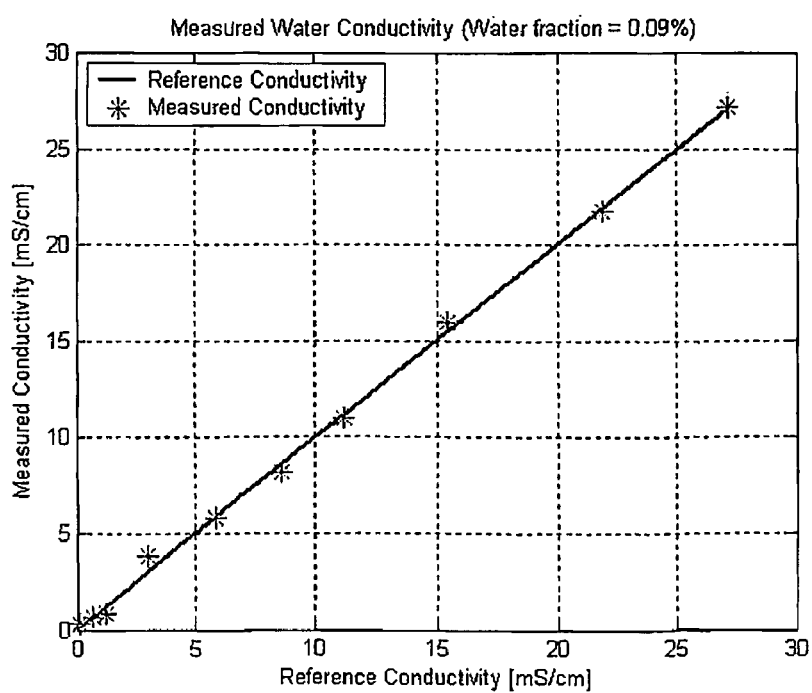
Figure 11:
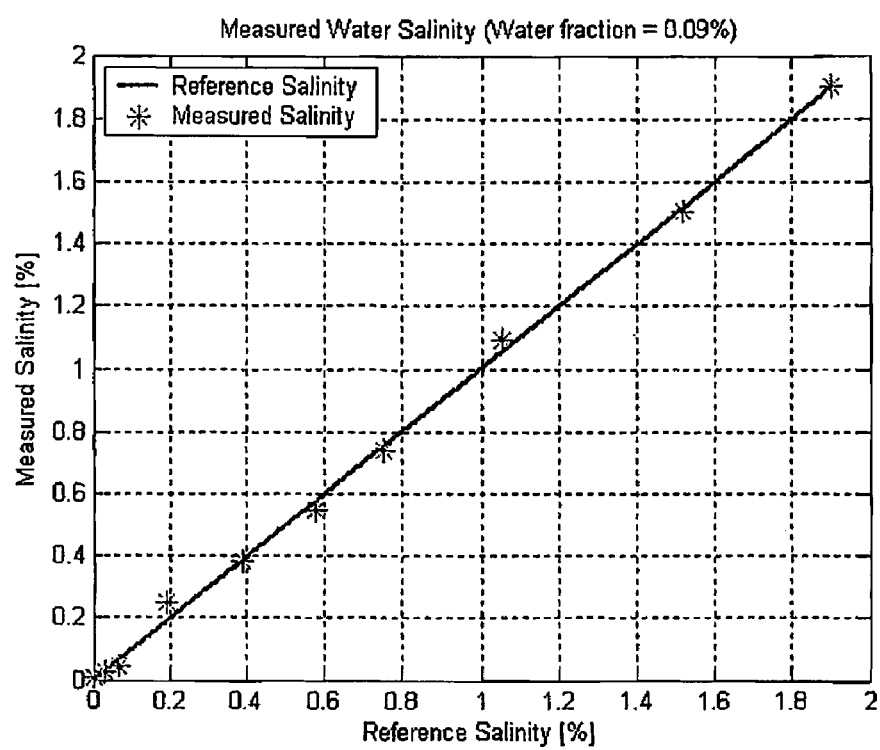

The invention will be further described in the following with reference to the figures, where:

FIG. 1 shows a schematic longitudinal sectional view of an exemplified embodiment of a meter for measuring the composition and water salinity according to the invention, FIG. 2 shows a schematic cross sectional view along the line III-III in FIG. 1, FIG. 3 shows a graph of the real and imaginary part of the dielectric constant for water, FIG. 4 shows a graph of the imaginary part of the dielectric constant for water normalized to the values for fresh water, FIG. 5 shows a graph of the phase measurements in fresh and saline water, FIG. 6 shows a graph of the measured and theoretical effective and imaginary dielectric constant for water, FIG. 7 shows a graph of the phase measurements of a typical wet gas stream, FIG. 8 shows a graph of the measured water fraction of a typical wet gas stream, FIG. 9 shows a graph of the measured s-factor vs. the imaginary dielectric constant for water, FIG. 10 shows a graph of the measured conductivity vs. the theoretical conductivity of the water fraction, and FIG. 11 shows a graph of the measured salinity vs. the theoretical salinity of the water fraction.

The exemplifying composition meter according to the invention shown in FIG. 1 includes three main elements as follows:

1) The effective dielectric constant, as defined below, of the multiphase mixture is derived by performing phase measurements over a wide frequency band. A RF signal is transmitted from a sending antenna 3 (probe) and received at two receiving antenna 4 located in a pipe 1 wherein a mixture of oil, water and gas is flowing. The pipe and antenna arrangement of FIG. 1 may also be referred to as a sensor. The frequency of the RF signal is typically varied from 10 Mhz to 3.500 Mhz. For pipes or venturi throats with an inner diameter below 50 mm, the upper frequency may be as high as 10.000 Mhz. By recording the frequency at several predetermined phase differences and using a calibration constant for the system, the effective dielectric constant within the pipe can be measured.

2) The imaginary part of the dielectric constant of the multiphase mixture is derived by measuring a parameter called the S-factor (shape factor) of the phase difference vs. frequency. The S-factor is here defined as the measured frequency difference at a upper and lower predetermined phase difference divided by the measured frequency at a predetermined phase difference in between the upper and lower phase difference. By using a calibration constant for the system, the imaginary part of the dielectric constant of the multiphase mixture can be derived.

3) Based on a determination of temperature, pressure and density and knowledge of the effective and imaginary dielectric constant and density of oil, gas and water, the fraction of oil, gas and water and the salinity of the water can be derived.

The effective dielectric constant is defined as:

$$\in_{eff} = \sqrt{(\in')^2 + (\in'')^2}$$

Where:

$\in'$: Real part of dielectric constant $\in''$: Imaginary part of dielectric constant Instruments for measuring temperature, pressure and density can be included in the composition meter for determining the temperature, pressure and density. Alternatively, the temperature, pressure and density can obtained from other sources such as temperature and pressure transmitters located upstream or downstream the composition meter and transferred electronically to the composition meter. The density of the flowing fluid through the composition meter can also be determined using PVT (Pressure, Volume and Temperature) algorithms. Based on the composition of the hydrocarbons and the measured water fraction from the composition meter, the multiphase mixture density can then be calculated in an iterative process based on equations of state for hydrocarbons as a function of temperature and pressure and the measured water fraction.

Disadvantages with the existing solutions.

It is well known that the complex dielectric constant of a media can be measured by measuring the phase shift and attenuation of an electromagnetic wave through the media. The main disadvantage of such solutions for measurement of complex dielectric constant is that they have limited accuracy and are unable to sense small variations since they rely on an accurate power or loss measurement. Accurate power and loss measurements at microwave frequencies are difficult to perform partly due to impedance mismatch, which is very common for any microwave based industrial device for measuring dielectric constant, and partly due to limitations of the electronics itself. Consequently, the limitations of the measurement electronics and standing waves due to impedance mismatches makes it difficult to obtain the required accuracy, repeatability and sensitivity for accurate composition and water salinity measurement for wetgas wells and crude oil wells with high gas fractions where it is critical to perform accurate measurements of small fluctuations in the water fraction and salinity.

Uniqueness of the present invention.

The uniqueness of the invention is the ability to provide accurate, repeatable measurements of the complex dielectric constant and its ability to sense small variations in the complex dielectric constant without the need to perform any power and/or loss measurements. Instead the complex dielectric constant is measured based on a differential measurement of phase and measurement of frequency where highly accurate measurements can be performed since the phase is far less affected by impedance miss matches compared to power/loss measurements. Also, any discrepancies in the sensor, cable and electronic measurement paths can easily be removed by using the same physical length of both paths. Hence, the present invention is far less affected by measurement distortions related to power variations in the frequency spectrum and standing waves (rippel) in the measurement electronics sensor arrangement compared to techniques based on measurement of electrical power and/or electrical loss.

DETAILED DESCRIPTION OF THE INNOVATION

The lowest cut-off frequency of a circular wave guide is $TE_{11}$ at:

$$f_c = \frac{0.293}{r\sqrt{\mu\varepsilon}} \quad \text{Equation 1}$$

where:

$f_c$=Cut-off frequency r=Radius of pipe $\in$=Effective Dielectric constant (permittivity) inside the wave guide (pipe)

$\mu$=Permeability inside the wave guide (pipe)

Below the cut-off frequency, the electric field will propagate according to plane wave theory. When the field in the pipe 1 changes from plane wave propagation into $TE_{11}$, a step occurs in the phase difference of the receiving probes 4 of FIG. 1. By applying a frequency sweep on the transmitter 3 and measuring the frequency location of the phase shift 25, the cutoff frequency $f_c$. Equation 1 can be rearranged as:

$$\varepsilon = \frac{k_2^2}{f_c} \qquad \text{Equation 2}$$

where:

$$k_2 = \frac{0.293}{r\sqrt{\mu}}$$

$f_c$=Frequency of electromagnetic wave (cut-off frequency of $TE_{11}$)
∈=Effective dielectric constant inside the pipe hence $k_2$ can be determined by measuring the frequency $f_c$ with a known dielectric constant inside the pipe.

It is well known that the real and imaginary parts of the dielectric constant can be described as:

$$\in = \in' - j\in'' \qquad \text{Equation 3}$$

where:
∈=Complex dielectric constant
∈'=Real part of the complex dielectric constant
∈''=Imaginary part of the complex dielectric constant For air, gas, oil and condensate, the imaginary part of the dielectric constant is for all practical purposes zero. For water, the complex dielectric constant can be described by a single Debye relaxation law where:

$$\varepsilon_{water} = \varepsilon_\infty + \frac{\varepsilon_s - \varepsilon_\infty}{1 + \left(j\frac{\omega}{\omega_r}\right)^{1-\eta}} - j\frac{\sigma_{water}}{\omega\varepsilon_0} \qquad \text{Equation 4}$$

where:
∈$_{water}$=Complex dielectric constant of water
∈$_\infty$=Dielectric constant at infinite frequencies
∈$_s$=Static dielectric constant
ω=Frequency
ω$_r$=Debye relaxation frequency
η=Cole-Cole spread factor
σ$_{water}$=Conductivity of water
∈$_0$=Boltzmann's constant According to J. B. Hasted, *Aqueous Dielectrics* (1973), page 29, the dielectric constant of water may also be described as:

$$\varepsilon_{water} = \varepsilon_s - j\left(\varepsilon''_{dielectric} + \frac{\sigma_{water}}{\omega\varepsilon_0}\right) \qquad \text{Equation 5}$$

where:
∈$_{water}$=Complex dielectric constant of water
∈$_s$=Static dielectric constant
∈''$_{dielectric}$=Imaginary part of dielectric constant for fresh water
σ$_{water}$=Conductivity of water
ω=Frequency
∈$_0$=Boltzmann's constant Measurements and equations of the static dielectric constant of water and the imaginary part of the dielectric constant for fresh water are well described in the literature. Some examples are Malmberg and Maryott (1956), *Res. Nat. Bur Standards*, 56, 1 (static dielectric constant), Åkelöf and Oshry (1950) *Am. Chem Soc*, 72 284 (static dielectric constant), Barthel (1991), *Phys. Chem*, 95, p 853 (imaginary dielectric constant for fresh water) and Meissner and Wentz, *Report from Boeing/AER inverstigation for CMIS* (imaginary dielectric constant for fresh water).

FIG. 3 shows a graph the real 6 and imaginary 7 part of the dielectric constant of fresh water and the imaginary part of saline water 8, 9, 10, 11, 12 at 25° C. with a salinity of 0.5%, 1.0%, 1.5% and 2.0% NaCl by weight respectively. FIG. 4 shows the same data for the imaginary part of saline water 13, 14, 15, 16, 17 with a salinity of 0.5%, 1.0%, 1.5% and 2.0% NaCl by weight respectively, normalized to the value of the imaginary part of the dielectric constant for fresh water.

FIG. 5 shows the phase difference 18, 19, 20, 21, 22 when the sensor of FIG. 1 is filled with 100% water with a salinity of 0.0%, 0.05%, 0.10%, 0.15% and 0.20% NaCl by weight respectively. FIG. 5 shows the corresponding measurement of the effective dielectric constant 23 and imaginary part 24 of the dielectric constant vs. the theoretical values.

FIG. 7 shows the phase measurement at a typical wetgas situation. Initial, the sensor is empty with a response as shown in 25. When 0.09% fresh water is injected into the sensor, the phase difference curve 26 shits approximately 4.5 Mhz to the left. Furthermore, as the salinity of the water is increased to 0.5%, 1.0%, 1.5% and 2.0% NaCl by weight respectively, the slope of the phase curve 27, 28, 29, 30 is reduced as seen in FIG. 7.

In order to measure the composition of oil, water and gas (% oil, % water & % gas), the following equations can be used based on a measurement of the mixture dielectric constant ∈$_{mix}$ and the mixture density ρ$_{mix}$:

$$\Phi_{oil} + \Phi_{water} + \Phi_{gas} = 1 \qquad \text{Equation 6}$$

where:
Φ$_{oil}$=Cross sectional volume fraction of oil(or condensate)
Φ$_{water}$=Cross sectional volume fraction of water
Φ$_{gas}$=Cross sectional volume fraction of gas $$\Phi_{oil} \times \rho_{oil} + \Phi_{water} \times \rho_{water} + \Phi_{gas} \times \rho_{gas} = \rho_{mix} \qquad \text{Equation 7}$$

where:
ρ$_{oil}$=Density of oil (or condensate)
ρ$_{water}$=Density of water
ρ$_{gas}$=Density of gas
ρ$_{mix}$=Measured density A temperature and pressure measurement is also required in order to compensate the above density parameters for temperature and pressure variations but, for simplicity, these will be ignored for the following discussions of the measurement principle.

The Bruggeman-Hanai mixing equation relates the dielectric constant of a two component mixture to the volume fractions of the components. If the two component mixture is droplets as an inner phase dispersed in a continuous media of an outer phase, the equation become:

$$\frac{\varepsilon_{inner} - \varepsilon_{mix}}{\varepsilon_{inner} - \varepsilon_{outer}} * \left(\frac{\varepsilon_{outer}}{\varepsilon_{mix}}\right)^{\frac{1}{3}} = 1 - \frac{\phi_{inner}}{\phi_{inner} + \varphi_{outer}} \qquad \text{Equation 8}$$

where:
∈$_{inner}$=Dielectric constant of the inner phase (dispersed phase)
∈$_{outer}$=Dielectric constant of the outer phase (continuous phase)
∈$_{mix}$=Measured dielectric constant of the mixture $\Phi_{inner}$=Volume fraction of inner phase (dispersed phase)
$\Phi_{outer}$=Volume fraction of outer phase (continuous phase)

A temperature and pressure measurement is also required in order to compensate the above dielectric constant parameters for temperature and pressure variations but, for simplicity, these will be ignored for the following discussions of the measurement principle.

The equation above can also be used for a three-phase mixture such as oil, water and gas in which the inner phase is a well mixed combination of two of the phases dispersed in an outer phase. E.g., an inner oil/water mixture may be dispersed in an outer continuous media of gas and similarly, gas bubbles may be dispersed in an outer continuous media of an oil/water mixture.

FIG. 8 shows the measured water fraction of the raw measurements of FIG. 7. The dielectric constant is calculated based on equation 1 and 2 and the volume fraction of the water fraction is calculated based on equation 8.

The imaginary part of the dielectric constant of the multiphase mixture is derived by measuring a parameter called the S-factor (shape factor) of the phase difference vs. frequency. The S-factor is here defined as the measured frequency difference at a upper and lower predetermined phase difference divided by the measured frequency at a predetermined phase difference in between the upper and lower phase difference.

FIG. 9 shows the measured normalized S-factor of the data of FIG. 6 vs. the normalized imaginary part of the dielectric constant for water. The data is normalized to the corresponding values for fresh water. By applying an experimental derived correction factor to the normalized S-factor measurement, the conductivity, and thereby salinity, of the water fraction can be measured. One way to experimentally obtain the correction factor above is to circulate gas or air with a known water content and known water salinity through the sensor and record the corresponding S-factor measurements. By adjusting the amount of gas, water and water salinity of the fluid mixture circulating through the sensor, the correction factor(s) can be derived for a wide operational range of the composition meter.

FIG. 10 shows the measured water conductivity of the water fraction vs. the reference conductivity and FIG. 11 shows the measured water salinity vs. the reference salinity of the raw data measurement of FIG. 7.

Since the salinity of the formation water is known to the field operator, the formation water fraction and fresh water fraction can be calculated based on the above measurements of the total water fraction and water fraction salinity.

The invention claimed is:

1. A method for determining the composition and water salinity of a multi-component mixture of a gas and at least one liquid, including water, in a pipe conducting a wet gas well stream, the method comprising the following steps:
   a. electromagnetic phase measurements are performed between two receiving antennas located at different distances from a sending antenna,
   b. based on an empirically determined constant(s) and the above measurements, the effective and imaginary dielectric constants are determined,
   c. the mixture density is determined,
   d. the temperature and pressure are determined,
   e. based on the knowledge of densities, effective dielectric constants and imaginary dielectric constants of the components of the fluid mixture and the results of the above steps a-d, the volume fractions of the gas and liquid or liquids of the fluid mixture and salinity of the water are calculated;

wherein the electromagnetic phase measurements are performed by doing a frequency sweep on a transmitting antenna and measuring the frequency at at least three pre-determined phase differences on the two receiving antennas.

2. A method according to claim 1, wherein the electromagnetic measurements are performed in a frequency range between 10 Mhz and 10.000 Mhz.

3. A method according to claim 1, wherein the electromagnetic phase measurements are performed in the cross sectional direction of the pipe.

4. A method according to claim 1, wherein the determined effective dielectric constant is calculated based on the average of the measured frequencies at said at least three predetermined phase differences.

5. A method according to claim 1, wherein the imaginary part of the dielectric constant is determined based on the frequency difference between two of said measured frequencies and a frequency there between.

6. A method according to any one of claims 1, 2 or 3, wherein the mass fractions of the fluid mixture are calculated.

7. An apparatus for measuring the composition and water salinity of a fluid multi-component mixture of gas and at least one liquid, including water, in a pipe conducting a wet gas well stream, the apparatus comprising a tubular section and the following elements:
   a. means for performing electromagnetic phase measurements between two receiving antennas located at different distances from a sending antenna,
   b. a computer and a mathematical program for calculating the effective and imaginary dielectric constants based on the above measurement and at least one empirically determined constant,
   c. means for determining the mixture density,
   d. means for determining the temperature and pressure,
   e. means for calculating the volume fractions of the gas and liquid or liquids of the fluid mixture and salinity of the water based on the knowledge of densities and effective and imaginary dielectric constants of the components of the fluid mixture and the results determined by the above means a-d, and
   f. electronic means for transmitting a frequency sweep on at least one transmitting antenna at the time and recording the phase difference for the frequency sweep on at least two receiving antennas.

8. An apparatus according to claims 7, wherein the tubular section comprises at least one transmitting antenna and at least two receiving antennas located in substantially the same cross section of the tubular section.

9. An apparatus according to any one of claims 7 or 8, comprising a densitometer based on Y-ray absorption for measuring density of the fluid mixture.

10. An apparatus according to any one of claims 7 or 8, comprising a computer, mathematical program and compositional description of the hydrocarbons for calculating the density of the fluid mixture.

11. A method according to claim 2, wherein the electromagnetic phase measurements are performed in the cross sectional direction of the pipe.

12. A method according to claim 11, wherein the electromagnetic phase measurements are performed by doing a frequency sweep on a transmitting antenna and measuring the frequency at at least three pre-determined phase differences on the two receiving antennas.

13. A method according to claim 12, wherein the determined effective dielectric constant is calculated based on the average of the measured frequencies at said at least three predetermined phase differences.

14. A method according to claim 12, wherein the imaginary part of the dielectric constant is determined based on the frequency difference between two of said measured frequencies and a frequency there between.

15. A method according to claim 12, wherein the mass fractions of the fluid mixture are calculated.

* * * * *